United States Patent [19]

Fischer et al.

[11] Patent Number: 5,187,071

[45] Date of Patent: Feb. 16, 1993

[54] METHOD FOR THE SELECTIVE CONTROL OF WEEDS, PESTS, AND MICROBES

[76] Inventors: Randy S. Fischer, 3746 NW. 7th Ave., Gainesville, Fla. 32607; Roy A. Jensen, P.O. Box 1460, Melrose, Fla. 32666

[21] Appl. No.: 219,959

[22] Filed: Jul. 15, 1988

[51] Int. Cl.$^5$ ............................................. C12Q 1/18
[52] U.S. Cl. ........................................ 435/32; 435/29; 514/76; 514/119; 424/9
[58] Field of Search ................... 435/29, 32; 424/404, 424/405, 9; 514/76, 119

[56] References Cited

PUBLICATIONS

Press et al–Chem. Abst. vol. 99 (1983) p. 207996u.
Amrhein et al–Chem. Abst. vol. 96 (1982) p. 81196a.
Rees et al–Chem. Abst. vol. 104 (1986) p. 104,222f.
Rupp et al–Chem. Abst. vol. 103 (1985) p. 118,156d.
Chemical Abstracts 11th Collective Index General Subjects–vol. 96–105 (1982–1986) pp. 20480GS–20483GS.
Chemical Abstracts vol. 96–105 General Subject Index (1982–1986) pp. 24175GS to 24178GS.
Marr et al. 1978. Antitrypanosomal Effect of Allofurinol: Conversion in Vivo to Aminopyrazolopyrimidine Nucleotides by Trypanosoma . . . Science 201:1018.
Larossa et al. 1984. Amino Acid Biosynthetic Enzymes as Targets of Herbicide Action. Trends in Biotechnol. 2 158.
Jensen et al. May, 1987. The Postprephenate Biochemical Pathways to Phenylalanine & Tyrosine: An Overview. Meth. Enzymol. 142 472.
Whitaker et al. 1984. Clues from *Xanthomonas campestris* about the Evolution of Aromatic Biosynthesis . . . J. Mol. Evol. 21 139.
Berry et al. 1987. Enzymatic Arrangement and Allosteric Regulation of Aromatic Amino Acid Pathway in Neisseria . . . Arch. Microbiol. 149 87.
Fischer et al. 1986. Comparative Action of Glyphosate as a Trigger of Energy Drain in Eubacteria. J. Bact. 168 1147.

*Primary Examiner*—Sam Rosen
*Attorney, Agent, or Firm*—Saliwanchik & Saliwanchik

[57] ABSTRACT

A novel means for identifying selective control agents for weeds, pests, and microbes is provided. Novel compositions for the selective control of weeds, pests, and microbes are also provided. The critical elements in the novel method of the invention relate to the systematic and specific identification of points of diversity which exist between the target organism and the host or other non-target organisms. More specifically the process involves identifying a difference which exists between the metabolic pathway of a microbial or plant target organism and a non-target host specie and then preparing a control agent which perturbs the metabolic pathway of the target without significantly perturbing the metabolic pathway of the host.

11 Claims, 1 Drawing Sheet

250 # METHOD FOR THE SELECTIVE CONTROL OF WEEDS, PESTS, AND MICROBES

BACKGROUND OF THE INVENTION

Chemists, microbiologists, and other scientists, as well as businesses and universities, spend a great deal of time and money in the search for chemical compounds which possess herbicidal, pesticidal, or microbicidal activity. Unfortunately, this search for new control agents often proceeds very slowly and cannot keep up with the demands of agriculture, veterinary medicine, and human medicine. One reason the process of identifying and isolating control agents does not move forward more rapidly is that there has been a lack of a dependable, predictable procedure which could be followed in order to arrive at the desired control agents.

Problems which have been encountered in the search for control agents for microbial plant pathogens are typical of the roadblocks researchers in other fields have encountered in their search for control agents. The development of new bactericides suited to the control of plant disease has been minimal during the past 25 years (1983 Resolution of the American Phytopathological Society). Effective agricultural chemicals that are environmentally compatible, preferably systemic, and that are not harmful to humans or animals are high priority needs in agriculture.

Only a few products are available within the area of antimicrobials for plant disease control, and these have very serious limitations. Streptomycin (which is now in use for seed treatment) is plagued with regulatory problems. Also, development of resistance to streptomycin is a problem, as is its unsatisfactory spectrum of activity. Treatment with copper is ineffective, in part due to phytotoxicity.

Similarly, in the search for herbicidal compounds, researchers have not been able to keep up with the demands of agriculture. Even though many effective control agents are available and on the market, new resistant strains of weeds frequently necessitate the development of new herbicides.

The isolation, identification, and synthesis of new herbicides often proceeds slowly even where herbicides have previously existed for the target weed. This inability to produce new herbicides is due, in part, to a general lack of understanding as to how previous herbicides functioned. Traditionally, herbicides and many other pesticides have been isolated by following large-scale screening procedures. These procedures essentially involve treating target weeds with a tremendous variety of chemical compounds until a compound which kills or otherwise controls the plant is found.

The use of screening procedures to obtain control agents has at least three distinct disadvantages. First, it is largely trial and error. Thus it is difficult to determine when and if success will be achieved, and, therefore, a great deal of time and money can be wasted testing compounds which have no control properties, and which do not help lead the researchers toward a useful control agent. The second major drawback of screening procedures is that these procedures may not give researchers any information regarding how close they are to identifying an effective control agent. For example, the researcher may be testing a compound which does not show control properties but which would be an effective control agent if a simple chemical modification of the compound were made.

Finally, even when screening procedures are successful in identifying a control agent, often the researcher initially has very little, if any, idea as to how the newly found chemical compound exerts its herbicidal, pesticidal, or bactericidal effect. Therefore, significant research aimed at elucidating the mode of action of a new control agent is often required before additional related control agents can be identified.

The subject invention is a systematic process for identifying and producing herbicides, pesticides, and bactericides. The process focuses on the production of chemical agents which will disrupt the metabolism of the target weed, microbe, or pest. The use of antimetabolite compounds as control agents is not new. However, to the extent that antimetabolite agents have been used in medicine and agriculture in the past, they have been selected using inefficient screening procedures. The process disclosed herein has several important advantages over the "brute-strength" approach which has been used in the past. In particular, the disclosed process provides a scientific, predictable, means for identifying, isolating, and synthesizing new pesticides, herbicides, bactericides, and derivatives thereof. Advantageously, and unlike the traditional screening procedures, the disclosed method does not depend upon every property needed by the successful compound to be correct initially.

If a compound displays evidence of being an effective inhibitor but does not inhibit pure cultures of phytopathogen or does not work in the field, this does not mean that the compound must be abandoned as a possible control agent. Instead, the compound can be modified in an appropriate way to optimize that compound's pesticidal, herbicidal, or bactericidal properties. This is in contrast to screening where valuable compounds can be missed because some modifiable factor is not just right.

BRIEF SUMMARY OF THE INVENTION

Claimed here is a novel method for controlling weeds, pests, and microbes by selectively and specifically altering the metabolic processes of the target species. The invention is a three-step process which enables researchers to methodically and predictably identify and produce agents for the control of unwanted pests, weeds, and microbes.

The three steps of the invention described here are as follows:

(1) identifying a metabolic difference which exists between a target pest, microbe, or weed, and non-target plants or animals;
(2) identifying compounds which, because of said different metabolic characteristics, exert an effect on the metabolism of the target specie(s) but which have no adverse effect on non-target plants or animals; and
(3) where necessary for purposes of stability or transport or convenience of production, prepare suitable analog or derivative compounds.

The control agents created using the disclosed process are designed to specifically attack the target species without adversely affecting desirable microorganisms, plants, or animals.

DETAILED DESCRIPTION OF THE INVENTION

Figure 1:
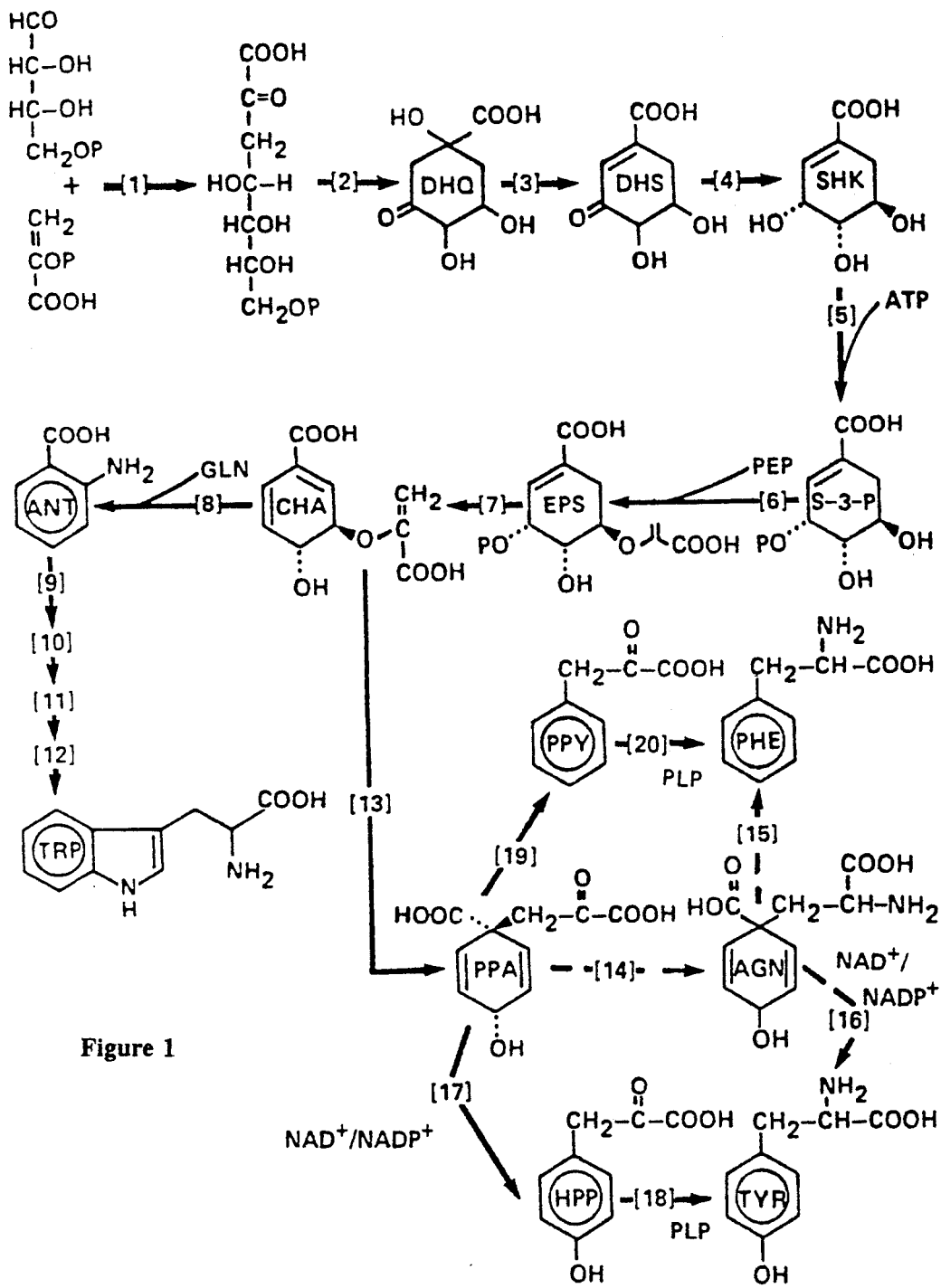

In nature there exists a great deal of diversity of metabolic processes. The subject invention relates to the specific, systematic exploitation of the diversity which exists amongst various species with respect to metabolic processes. Many pests, weeds, and undesirable microbes utilize metabolic pathways which are distinguishable from pathways of desired plants and animals. These unique pathways utilize biochemical repertoires, including enzymes, substrates and regulatory compounds, which do not happen to exist in non-target species, or at least are of minimal significance to these non-target species.

The disclosed process involves perturbing the unique biochemical process or component of the pest, weed, or microorganism. Because the pathway is unique, it is possible to perturb it with minimal effects on desired plants or animals which may be exposed to the treatment.

The claimed process can best be described in terms of its three principal steps. The first step in the claimed method involves the characterization of metabolic pathways in both the target species and non-target plants or animals. Once these pathways are characterized, unique aspects of the pathways can be identified.

The next step of the claimed process is a determination of how to effectively perturb the unique pathway of the target specie(s). For example, metabolic pathways can be disturbed by adding compounds which impact on a regulatory mechanism. This could be used to either shut down a critical pathway, or, conversely, to make the pathway overproduce, thus draining the energy reserves of the target organism and, possibly, creating a toxic buildup of end products or intermediates.

Generally, the exact compounds which naturally exist as components of an organism's biochemical pathways cannot be used as control agents for that target organism. This is because the organism is accustomed to the presence of that compound, and the organism can be expected to have biochemical means for handling an excess of the compound. Therefore, the final step in the claimed process is to create analogs of the appropriate metabolic compound(s). In order to create a suitable analog, first, the features of the normal inhibitor are assessed in order to determine which features are essential for inhibition. Based on this information it is possible to determine which moieties of the compound can be altered without adverse impact on inhibition. Then, further molecular modifications can be made to facilitate stability and permeation into appropriate cells. The analogs which are thus created must retain the ability to act in the desired capacity in the metabolic pathway and must be cost-effective to produce, stable, readily applied to the target specie(s) in appropriate concentrations, and able to enter the cells where they will have the desired effect.

Each of the three principal steps of the subject invention will now be discussed in detail.

Identification of a Target Metabolic Pathway

Although many living organism have similar metabolic pathways, recent research has demonstrated that significant metabolic diversity exists between different species. A particular metabolic pathway may be crucial for a given specie or group of species, but not exist at all for other species. Because of this diversity, a particular chemical compound may have a drastic effect on the metabolism of one specie but no effect at all on other species. This diversity provides an opportunity for selective disruption of the metabolism of a target specie(s) without disturbing other non-target species. The identification of specific differences in the metabolic processes of the target specie(s), as compared to non-target species, constitutes the first step in the subject invention.

Initially, the researcher must characterize the important metabolic pathways of the target organism. It is within the skill of a person trained in biochemistry to make the metabolic characterizations necessary to practice the subject invention. For purposes of this invention, the most important metabolic pathways are those which produce a large number of compounds or which are energy intensive. The crucial factor is that the metabolic pathway must be of sufficient importance to the target organism so that if the pathway is disturbed, the organism will be killed or controlled.

Next, the researcher must make an assessment of the metabolic pathways existing in non-target species that are likely to be exposed to the treatment. Once this has been done, it is possible to identify points of diversity which exist between the target specie(s) and non-target species. For example, a metabolic pathway which exists only in the target specie(s) and utilizes unique compounds or unique methods of regulatory control would provide suitable diversity for the design of a specific control agent. Also, a target organism and a non-target organism both may have a certain metabolic pathway but particular enzyme steps may differ. Such points of diversity provide targets for selective metabolic attack.

An example of such a unique biochemical target is the metabolic pathway known as the shikimate pathway of aromatic amino acid biosynthesis. This pathway is a complex, multi-branched biochemical network of central metabolic importance. The major endproducts are the three aromatic amino acids: L-phenylalanine, L-tyrosine, and L-tryptophan. A generalized representation of the aromatic amino acid pathway is provided in FIG. 1.

Referring to FIG. 1, enzymes [1–7] catalyze steps within the common shikimate branch; enzyme [13] catalyzes the single reaction of the midbranch; enzymes [8–12] and [14–20] catalyze terminal branchlet reactions culminating with L-tryptophan (TRP), L-phenylalanine (PHE), or L-tyrosine (TYR) synthesis. Only some organisms possess the entire array of dual branchlets to PHE and TYR, i.e., enzymes [14–20]. The dotted arrows show the arogenate branches of PHE and TYR biosynthesis. Enzymes [16] or [17] may be NAD-linked, NADP-linked, or both, depending on the organism. The pathway begins (upper left) with the condensation of erythrose-4-phosphate and phosphoenolpyruvate (PEP) to form 3-deoxy-D-arabinoheptulosonate 7-phosphate (DAHP). Other abbreviations: DHQ, dehydroquinate; DHS, dehydroshikimate; SHK, shikimate; S-3-P, shikimate-3-phosphate; EPSP, 5-enolpyruvylshikimate-3-phosphate; CHA, chorismate; ANT, anthranilate; GLN, glutamine; PPA, prephenate, AGN, L-arogenate; PPY, phenylpyruvate; HPP, 4-hydroxyphenylpyruvate; and PLP, pyridoxal-5' phosphate. Enzymes: [1], DAHP synthase; [2], dehydroquinate synthase; [3], dehydroquinase; [4], dehydroshikimate reductase; [5], shikimate kinase; [6], 5-enolpyruvylshikimate-3-phosphate synthase; [7], chorismate synthase; [8], anthranilate synthase; [9], anthranilate phosphoribosylpyrophosphate transferase; [10], phosphoribosyl anthranilate isomerase; [11], indoleglycerol phosphate synthase; [12], tryptophan synthase; [13], chorismate mutase; [14], prephenate aminotransferase; [15], arogenate dehydratase; [16], arogenate dehydrogenase; [17], prephenate dehydrogenase; [18], 4-hydroxyphenylpyruvate aminotransferase; [19], prephenate dehydratase; and [20], phenylpyruvate aminotransferase.

In addition to the production of aromatic amino acids, the shikimate pathway supplies a quantitatively minor but crucial output of beginning substrates needed for biosynthesis of folate, vitamin K, and ubiquinones. Points of departure for metabolic steps of catabolism or of secondary metabolism also originate from numerous shikimate pathway intermediates or end-products and are highly variable from organism to organism.

The aromatic amino acid pathway is generally present in prokaryotes and higher plants. However, this pathway does not exist within humans or other mammals. Enzymes which are crucial to the survival of microorganisms and plants having this metabolic pathway are absent from the biochemical network of mammals. Therefore, enzymes of aromatic amino acid biosynthesis offer ideal targets for attacking the metabolic processes of microorganisms and plants without affecting animals.

As exemplified by the aromatic amino acid pathway, identifying diversity in metabolic processes is the crucial factor in the initial step of the claimed invention. Metabolic diversity exists in a variety of forms. For example, bacteria are quite diverse with respect to relationships of carbon source to internal PEP levels and to aromatic pathway patterns of allostery. Thus, knowledge of aromatic pathway construction and regulation, as well as relationships with carbon metabolism, enhances prospects for designing antimicrobial strategies geared to a particular organism.

Although the aromatic amino acid pathway performs essentially the same function in each specie where it is present, there are a number of variations of the pathway in terms of intermediate compounds and forms of metabolic control. This diversity provides a basis for control strategies to be used against such major phytopathogens as species of Xanthomonas, Erwinia, and *Pseudomonas syringae*. Currently, no microbicide is available that is effective against these prokaryote phytopathogens.

Fortuitously, the aromatic amino acid pathway of these phytopathogens is distinguishable from the aromatic amino acid pathway utilized by plants. The differences between the aromatic amino acid pathways of plants and their phytopathogens provides an excellent opportunity to control the pathogen without adversely affecting the host plant. For example, *Xanthomonas campestris*, the bacterium which causes citrus canker, belongs to the sole bacterial grouping known to possess a unique pattern of allosteric control whereby sequentially acting circuits of feedback inhibition regulate aromatic biosynthesis. As discussed in Example 3, below, the unique aspects of this pathway can be exploited to design control agents for use specifically against this group of bacteria.

Erwinia species, such as *E. herbicola, E. carotovora, E. amylovora,* and *E. milletiae,* possess a bifunctional T-protein (chorismate mutase/prephenate dehydrogenase), a bifunctional P-protein (chorismate mutase/prephenate dehydratase) and a cyclohexadienyl dehydratase able to utilize either prephenate or L-arogenate as substrate. The T-protein dehydrogenase is capable of utilizing L-arogenate as an alternative substrate, but poorly. This arrangement of prephenate-utilizing enzymes is similar to that seen in *Xanthomonas campestris* and in *Pseudomonas syringae,* except that a cyclohexadienyl dehydrogenase is present instead of the T-protein.

In contrast to these major phytopathogens, higher plants use L-arogenate as a sole precursor of both phenylalanine and tyrosine. Neither arogenate dehydrogenase nor arogenate dehydratase are able to utilize prephenate as an alternative substrate. While bacteria exhibit very substantial diversity from one phylogenetic group to another, all the major plant pathogenic prokaryote groupings possess enzyme targets with similar vulnerabilities.

Thus, each of the three phytopathogenic groups possesses enzymes of phenylalanine and tyrosine biosynthesis that bind prephenate as the exclusive or favored substrate. Compounds that act as antimetabolite mimics of prephenate, but not of L-arogenate, can recognize the microbial enzymes as targets without affecting the arogenate-utilizing enzymes of higher plants.

The general biochemical dichotomy between plants and phytopathogenic bacteria provides a basis for obtaining a broad-spectrum agricultural chemical, while the diversity between pathogen groups allows room for specialized effects.

Broad-spectrum phytopathogen activity can be obtained because the enzyme targets under attack are present in most or all of the major crop pathogenic bacteria. Because each of the three phytopathogen bacterial groups has diverged from one another through evolutionary time, fortuitous changes in an enzyme target of one group may have created a basis for selective action against that group. For example, an antimicrobial chemical having selective action against species of Xanthomonas is a special-case possibility because of the unique regulatory role exerted by chorismate in this organism.

The general broad-specificity properties of the phytopathogenic enzymes suggest good potential for a number of structural analogs of prephenate to be effective control agents. It is also attractive that each organism possesses multiple enzyme targets for antimetabolite action. This increases chances for existence of at least one sensitive target, and the benefits of possible additive effects on multiple targets can be envisioned.

The claimed process can also be used to attack eukaryotic fungi because the aromatic pathway of these organisms uses exclusively prephenate-utilizing enzymes for aromatic biosynthesis.

From the foregoing discussion it should be evident that the biosynthesis of aromatic amino acids provides a metabolic target for the control of microorganisms without affecting animals. Furthermore, even amongst microorganisms there exist important metabolic differences with respect to the manufacture of aromatic amino acids. The shikimate pathway of aromatic amino acid biosynthesis is thus a particularly good example of an appropriate target for control agents which selectively disrupt the metabolism of the target pest, weed, or microorganism.

There are other metabolic pathways which also present attractive opportunities for the selective control of certain target species. In order for a metabolic pathway to be a viable candidate for selective attack, that pathway should be of sufficient significance to the target specie so that if the pathway is disturbed, then the organism will be harmed to the point where the desired level of control is achieved. Of course, it is possible to use the novel method of control disclosed here in connection with other forms of treatment, thus obviating the need for complete control to be achieved entirely by the disruption of the chosen metabolic pathway.

Two other examples of pathways which are potential targets for selective attack are: 1) the pathway leading to the biosynthesis of histidine, and 2) the pathway for the biosynthesis of the glutamate family of amino acids.

The histidine pathway is energy intensive because it starts with ATP and PRPP. Because the quantitative output by this pathway is normally very low, attack of mid-pathway enzymes causes a massive energy drain compared to what the organism usually invests. The histidine pathway is not present in humans or other animals; therefore, it provides an excellent target for selective control of microorganisms and weeds.

Although the glutamate pathway does exist in humans and other animals, there exist potential differences which may be exploited. In contrast to histidine production, glutamate production is normally quite high. The purine pathway also uses a large amount of energy. Mid-pathway attack of either of these pathways would create dramatic energy drain effects. Also, joint attack of these pathways, combined with attack of aromatic biosynthesis, can have a synergistic effect, thus increasing the efficiency of the control agent. L-arogenate is a novel analog of L-glutamate. Therefore, stable derivatives of arogenate could be used as antimetabolites of glutamates.

Yet another target for selective attack is the isoleucine/valine pathway. This multi-branched pathway is known to differ in particular steps in some organisms. For example, unique steps in this pathway exist in Leptospira, a human pathogen. The isoleucine/valine pathway connects with the leucine pathway. The enzymes of the leucine pathway are known to reorganize analogs of normal substrate quite well. Thus, there are many analog compounds which can be expected to be effective control agents for attack on this pathway.

Perturbing the Target Metabolic Pathway

The second step of the subject invention involves the determination of how to perturb the target metabolic pathway. There are at least three ways in which an antimetabolite can exert its deleterious effect on the target metabolic pathway. First, by interrupting the pathway, the plant or organism is deprived of the end product which would have been produced by the pathway. For example, if the aromatic amino acid pathway is disturbed, the end result will be starvation for essential aromatic amino acids.

Whether the antimetabolite exerts its influence in additional ways depends, to some extent, on the position in the pathway where the control agent attacks. For example, if the control agent perturbs the pathway by inhibiting mid-pathway enzyme activity, the plant or organism could suffer more than just the loss of a crucial end product. In particular, if an end product or other late-pathway compound acts as a feedback inhibitor for an early step in the pathway, then the absence of this inhibitor will prevent proper control of the pathway. Consequently, the initial stages of the pathway will not be shut down and the organism or plant will dedicate excessive energy to the disturbed pathway.

The resultant energy drain can be of great significance if the affected pathway utilizes an energy intensive process to make compounds or if the pathway is responsible for the production of a large quantity of compounds.

Yet another way in which perturbation of a metabolic pathway can harm an organism or plant is through a buildup of intermediate compounds which are toxic when present in high concentrations. The accumulation of intermediates can occur when a mid-pathway reaction has been inhibited. In such a case, the early pathway steps may proceed uninhibited thus causing a buildup of unreacted intermediate compounds.

The substrate ambiguity of some enzyme systems also raises the possibility that enzymatic conversion of a "false substrate" may form a product which could inhibit the next enzyme of the series. Thus, a more potent antimetabolite may be generated in vivo and/or a series of enzyme targets may be affected.

In order to optimally disrupt the target specie's metabolic processes, the researcher should focus on a compound which is not significant to the biochemistry of non-target species but will cause one of the aforementioned perturbations in the metabolic pathway of the target specie(s). Compounds which interfere with feedback inhibition mechanisms are especially attractive control agents because they can deprive the target organism of vital compounds and cause an energy drain. This combination of biochemical disruptions can be very effective in bringing about the rapid demise of the target organism.

Production of Suitable Analogs and Derivatives

Once the first two steps of the subject invention are completed, the researcher will have identified chemical compounds which can interfere with particular metabolic pathways. Often, such compounds are not stable and are difficult or costly to produce. In order to have a practical control agent, it is necessary to identify compounds which can be produced on a commercial basis and which can be stored and applied without chemical degradation.

Derivatives of pathway intermediates that are uniquely effective against phytopathogens and that mimic the natural compounds in their metabolic roles as substrate and/or allosteric agents can be prepared. Chemical modifications are oriented to objectives of obtaining control agents which exhibit stability and transportability into cells, while retaining their selective phytopathogenicity. Antimicrobial chemicals that act as irreversible inhibitors of enzymes are especially desirable.

New derivatives designed as enzyme inhibitors can be tested for ability to inhibit growth of phytopathogenic species. This testing is accomplished by use of agar disc diffusion methodology. In addition, rapidly growing suspension cell cultures of *Nicotiana silvestris* (which require aromatic amino acids for the primary growth process) can be used as a sensitive test system to monitor lack of phytotoxicity for the plants.

Successful antimetabolite derivatives of chorismate or prephenate must be intrinsically more stable than the parent molecules, at least prior to entry into the microenvironment of the cell. Esterification at the 1-carboxyl and/or replacement of the 4-OH function with a halide exemplify alterations that stabilize prephenate by hindering the mechanism of decomposition.

A single modification of prephenate such as appropriate modification of the 1-carboxyl could enhance transport or cell membranes and could stabilize the molecule, while not affecting the compound's ability to act as an antimetabolite of prephenate with respect to microbial prephenate dehydratase and/or prephenate dehydrogenase. Such an analog of prephenate would still be ignored by, or not accessible to, plant prephenate aminotransferase.

Chorismate and prephenate appear to be transported poorly into bacterial cells and have not been generally used as nutrients, e.g., to satisfy early-pathway enzyme defects of mutants. Formation of an ester derivative at the 1-carboxyl (and maybe the sidechain carboxyl as well) would assist transport by decreasing the charge of the molecule. Once transported into cells, the complement of esterases inevitably present in cells would restore the original carboxyl moiety.

If retention of the ester intracellularly is desired, particular ester derivatives could be sought that resist esterase action. Another approach would be to join cyclohexadienyl compounds in amide linkage to readily transportable amino acids such as L-leucine. Such amide bonds of molecules would be successfully transported into cells to be attacked by ubiquitous peptidases, regenerating the original molecules.

Following are examples which illustrate the novel process, including the best mode, of the invention claimed here. These examples are illustrative and should not be construed as limiting this pioneer concept.

EXAMPLE 1

Preparation of an Herbicide

The first step in practicing the subject invention to identify an herbicide which is not toxic to beneficial microorganisms, humans or animals is to identify a metabolic pathway which is utilized by the target plants but which does not exist in humans or animals.

The aromatic amino acid pathway is such a metabolic target. This pathway provides a source of enzyme targets for the design of new herbicides. In higher plants the aromatic pathway is striking for the sheer quantitative flow of carbon molecules that pass through it on the way to an equally striking variety of secondary metabolites. Because mammals lack the aromatic amino acid pathway altogether, problems of long-term toxicity for animals or man ingesting crop plants are not expected.

Step two of the process requires the determination of specific vulnerable points of attack in the target pathway. The version of the aromatic amino acid pathway which exists in plants provides suitable points of attack. L-arogenate is recognized as the major or exclusive precursor of L-tyrosine and L-phenylalanine in higher plants. Because lignins and an enormous array of phenylpropanoid compounds are derived from aromatic amino acids, up to 60% of the dry weight of higher plants is represented by molecules that are derivative of L-arogenate. Therefore, it is evident that a disturbance of this pathway would have a devastating effect on the plant as a whole.

In higher-plant chloroplasts L-arogenate is a regulatory molecule (feedback inhibitor) for 3-deoxy-D-arabino-heptulosonate 7-phosphate synthase, the initial enzyme of aromatic amino acid biosynthesis. Because L-arogenate regulates aromatic amino acid biosynthesis in the chloroplast by feedback inhibition exerted upon the initial enzyme of aromatic biosynthesis, it provides an excellent point of attack. Application of L-arogenate or an L-arogenate-type compound will cause a serious disturbance of the feedback inhibition mechanism of this crucial metabolic pathway.

The final step of the claimed process requires the production of analogs or derivatives of the compound(s) identified in step two. L-arogenate can be prepared enzymatically and by chemical synthesis. Also, L-arogenate can be isolated from the culture supernatants of a multiply-blocked mutant of *Neurospora crassa*. This *Neurospora crassa* is publicly available from the American Type Culture Collection (ATCC) 12301 Parklawn Drive, Rockville, Md. 20852 U.S.A. The deposit has an accession number of ATCC 36373. This method consists of a series of anion-exchange chromatography steps at several pH conditions followed by a final desalting purification via gel filtration (Jensen, R. A., L. Zamir, M. St. Pierre, N. Patel, and D. L. Pierson [1977] "Isolation and Preparation of Pretyrosine, Accumulated as a Dead-End Metabolite by *Neurospora crassa*," J. Bacteriol. 132:896–903; Zamir, L. O., E. Jung, and R. A. Jensen [1983] "Co-accumulation of Prephenate, L-Arogenate and Spiro-Arogenate in *Neurospora*," J. Biol. Chem. 258:6492–6496). L-arogenate can be detected and quantitated by dansylation and subsequent thin-layer chromatography (TLC) on polyamide plates (Zamir, Jung, and Jensen [1983] supra) or by derivatization with o-pthalaldehyde (OPA) followed by separation on a reverse-phase HPLC column (Zamir, L. O., R. Tiberia, M. Fiske, A. Berry, and R. A. Jensen [1985] "Enzymatic and Non-Enzymatic Dehydration Reactions of L-Arogenate," Biochemistry 24:1607–1612).

High-performance liquid chromatography (HPLC) procedures have also been used to provide analytical quantities of high-purity L-arogenate from preparations initially isolated from *N. crassa* by the above method (Zamir, L. O., R. Tiberia, E. Jung, and R. A. Jensen [1983]"Isolation and Structure Determination of a Novel Spiro-Gamma-Lactam: Spiro-Arogenate," J. Biol. Chem. 258:6486–6491; Connelly, J. A. and D. L. Siehl [1987] "Purification of Chorismate, Prephenate, and Arogenate by HPLC," In: *Methods in Enzymology* (S. Kaufman, ed.), Vol. 142:422–431).

Because L-arogenate is an amino acid, it should be transported readily into plant cells and their subcellular compartments. Chemical modification of L-arogenate would be geared to stabilization against acid-lability of the molecule, at the same time maintaining molecular features critical for binding to the regulatory enzyme. Such modifications are within the skill of a person trained in biochemistry.

EXAMPLE 2

Identification and Preparation of a Control Agent for Group II Bacterial Phytopathogens Initially, in order to use the novel process to identify an agent which will control plant pathogens without adversely affecting the host plant, the researcher must locate a metabolic difference between the host plant and the target plant pathogen.

Group II pseudomonads, such as *Pseudomonas syringae* and *Pseudomonas cepacia*, are known to have identical patterns of enzyme expression and control within the aromatic pathway. Of particular interest in the present context is the arrangement of prephenate-utilizing enzymes. Enzymes of phenylalanine and tyrosine biosynthesis bind prephenate as the exclusive or favored substrate. This is in direct and significant contrast to the aromatic pathway in higher plants where L-arogenate is used as the sole precursor of both phenylalanine and tyrosine. Neither arogenate dehydrogenase nor arogenate dehydratase of higher plants are able to utilize prephenate as an alternative substrate. Therefore, compounds which mimic prephenate could disrupt the aromatic pathway of the phytopathogen without binding with the arogenate enzymes of the host plant.

Another enzyme known to be present in higher plants is prephenate aminotransferase. A control agent designed to interfere with the normal functioning of a phytopathogen's prephenate dehydrogenase and dehydratase must not interfere with the host plant's prephenate aminotransferase if the control agent is to be selective against the phytopathogen without harming the host plant. Advantageously, the prephenate aminotransferase of higher plants exhibits very high specificity for prephenate. It has also been found that most or all prephenate aminotransferase of such crops as sorghum, spinach, and tobacco is localized within the chloroplast compartment. Therefore, antimetabolites of prephenate within plant cells are fortuitously separated spatially from plant prephenate aminotransferase.

In contrast to the plant prephenate aminotransferase, the Group II pseudomonad's prephenate dehydrogenase and dehydratase are known to have broad specificity. Therefore, it can be expected that there are a number of structural analogs of prephenate which would bind to the microorganism's enzymes but which would not bind with the host plant's aminotransferase.

An analog of prephenate which has a modified 1-carboxyl substituent will not bind with the prephenate aminotransferase. Therefore, a prephenate analog having an altered sidechain would continue to bind with dehydrogenase and dehydratase of the microbial target but not with prephenate aminotransferase of the host plant. Prephenyllactate, which has been identified as β-(1-carboxyl-4-hydroxy-2,5-cyclohexadien-1-yl) lactic acid, is an analog of prephenate which meets these criteria.

It has been found that microbial prephenate dehydrogenase and cyclohexadienyl dehydrogenase utilize prephenyllactate as a substrate quite well. Also, it has been found that arogenate dehydrogenase enzymes do not use prephenyllactate as a substrate. Therefore, prephenyllactate is an appropriate prephenate analog for the control of phytopathogens.

Prephenyllactate can be obtained through genetic manipulation of the eukaryotic organism *Neurospora crassa*. *N. crassa* is able to accumulate a whole family of prephenate derivatives that are not ordinarily synthesized by the wild-type organism. When genetic blocks for genes encoding prephenate dehydratase and prephenate dehydrogenase are imposed, prephenate accumulates to high levels. Under these conditions, a variety of enzyme transformations occur as the result of hidden substrate ambiguity which only surfaces under manipulated conditions. Under these conditions, very substantial amounts of prephenyllactate are accumulated following enzymatic reduction of the prephenate sidechain.

Prephenyllactate can be isolated from the *N. crassa* as described in Zamir, L. O., R. A. Jensen, B. H. Arison, A. W. Douglas, G. Albers-Schonberg, and J. R. Bowen [1980] "Structure of Arogenate (Pretyrosine), an Amino Acid Intermediate of Aromatic Biosynthesis," J. Amer. Chem. Soc. 102:4499-4504; Jensen et al. [1977] supra; and Zamir, Jung, and Jensen [1983] supra.

EXAMPLE 3

Identification and Preparation of a Control Agent for *Xanthomonas campestris*

Xanthomonad bacteria belong to a cohesive phylogenetic assemblage of prokaryotes denoted Group-V pseudomonads. *Xanthomonas campestris* is responsible for the economically important disease known as citrus canker. The phylogenetic cluster of Group-V pseudomonads (Xanthomonas) possess an intact biochemical pathway for biosynthesis of the three aromatic amino acids: L-tryptophan, L-tyrosine, and L-phenylalanine. They are the sole bacterial grouping known to possess a unique pattern of allosteric control whereby sequentially acting circuits of feedback inhibition regulate aromatic biosynthesis. This unique aspect of the bacteria's biochemistry provides the diversity necessary to satisfy step one of the novel invention and allows the researcher to proceed with the determination of specific vulnerable points in the pathway.

The early amino acid pathway circuit entails the feedback inhibition of 3-deoxy-D-arabinoheptulosonate 7-P (DAHP) synthase by chorismate. Thus, the DAHP synthase of Xanthomonas offers unique target of vulnerability in nature since an appropriate analog mimic of chorismate produces false feedback inhibition of DAHP synthase in Xanthomonas but not in the higher plant host. DAHP synthase in higher plants exists as two separately compartmented isozymes, neither sensitive to inhibition by chorismate. Hence, analog mimics of chorismate cause false feedback inhibition of DAHP synthase in Xanthomonas, but not in the plant host. Step two of the claimed process has thus been completed.

Chorismate derivatives having good feedback-mimicry properties against DAHP synthase also must be stable and permeable to Xanthomonas cells. Chorismate is unstable and does not transport well into microbial cells. In order to improve transport into the cells chemical modifications can be performed. One such modification is the formation of an ester derivative at the 1-carboxyl. Formation of an ester derivative at the sidechain carboxyl can also be carried out. These modifications assist transport of chorismate by decreasing the charge of the molecule.

Once transported into the cells the complement of esterases inevitably present in cells restore the original carboxyl moiety. If retention of the ester intracellularly is desired, particular ester derivatives could be sought that resist esterase action.

Derivatives of chorismate that possess alkylating functions can also be produced. These compounds act as irreversible inhibitors of DAHP synthase.

EXAMPLE 4

The DAHP synthase of xanthomonads is also sensitive to inhibition by L-tryptophan. Although chorismate is a primary regulatory molecule in vivo, the Ki values for inhibition by L-tryptophan are 0.44 mM and 0.58 mM with respect to PEP and erythrose-4-P—these values compare to Ki values for inhibition by chorismate of 0.40 mM (PEP) and 0.10 mM (erythrose-4-P). The DAHP synthase isozymes of higher plants are not affected by L-tryptophan. Thus, analog mimics of L- tryptophan attack a second site within the basic DAHP synthase target of Xanthomonas.

Derivatives of L-tryptophan could be produced in the same manner as those for chorismate, as outlined in Example 3 above. Analogs of chorismate can be used in conjunction with analogs of tryptophan to create an enhanced control through the synergistic effects of the two agents.

EXAMPLE 5

Analogs of chorismate can be used in conjunction with analogs of prephenate to create an enhanced control through the synergistic effects of the two agents. For example, a reduction by chorismate analogs of early-pathway flow would reduce intracellular prephenate concentration, thus increasing vulnerability to antimetabolite mimics of prephenate.

EXAMPLE 6

Members of the genus Neisseria inhabit the mucosal surfaces of warm-blooded animals. *N. gonorrhoeae*, the causative agent of gonorrhea, is an obligate human pathogen which can produce symptomatic or asymptomatic infections at a variety of tissue sites. Clinical manifestations, other than gonorrhoea, are arthritis, pharyngitis, pelvic inflammatory disease, and disseminated gonococcal infection.

*N. gonorrhoeae* has until recently been described as an aerobic organism containing high levels of cytochrome C oxidase. Recently it has been shown that *N. gonorrhoeae* grows anaerobically through use of nitrite as a terminal electron acceptor. Nitrite reductase is produced constitutively by gonococcal strains, and *N. gonorrhoeae* is able to make facile transitions between anaerobic/aerobic states of growth. Nitrite is present in biological fluids, and it appears that *N. gonorrhoeae* can grow anaerobically in the cervix, rectum, or oropharynx as sites of colonization.

Lactic acid, a common metabolite of human biological fluids, is readily utilized as a carbon and energy source in *N. gonorrhoeae*. It has been established that *N. gonorrhoeae* can convert phenyllactate (PL) and 4-hydroxyphenyllactate (HPL) to L-phenylalanine and L-tyrosine, respectively. HPL is a normal metabolite of tyrosine catabolism in human biological fluids. Thus, HPL, a natural host-tissue molecule, has been found to be transformed to a key regulatory molecule of tyrosine biosynthesis in *N. gonorrhoeae*. Also, PL may be present in occasional individuals as a reflection of the biochemical individuality that characterizes the highly heterozygous human population.

The enzymic basis for *N. gonorrhoeae*'s unusual ability to utilize PL and HPL has been shown to be the broad specificity of a membrane-bound lactate dehydrogenase (iLDH). The unusual broad specificity of *N. gonorrhoeae* [iLDH] suggests natural selection for the ability to oxidize a variety of lactyl derivatives encountered in the host-pathogen environment. Thus, [iLDH] has been implicated as an important element for pathogenesis, and is a prime target for antimetabolite attack.

Oxidation of HPL provides a source of tyrosine, an expensive molecule to synthesize, and initiates membrane energization in electron transport. An additional benefit of lactate oxidation to the organism is to render the immediate environment more anaerobic and better suited to the survival of the gonococcus.

The substrate ambiguity of the *N. gonorrhoeae* [iLDH] that enables it to use PL and HPL provides a target for the design of potent inhibitors of [iLDH] activity. Analog mimics that are not only very effective but also exceedingly selective against *N. gonorrhoeae* can be designed. In fact, the broad specificity indicates considerable latitude for the range of lactyl structures that may bind to [iLDH].

Success with the antimetabolite attack of aromatic pathway targets in *N. gonorrhoeae* can apply equally well to the closely related pathogen, *N. meningitidis*, the causative agent of acute bacterial meningitis. Even non-pathogenic species of Neisseria or Branhamella can be opportunistic pathogens in vulnerable host subjects.

EXAMPLE 7

Aromatic amino acid biosynthesis and regulation in *N. gonorrhoeae* has now been elucidated. It has been found that a basis exists both for attack of common targets and for attack of selective targets.

Neisseria is unusual in its utilization of 4-hydroxyphenylpyruvate as an inhibitor of prephenate/arogenate dehydrogenase. The unusual inhibition of prephenate dehydrogenase in *N. gonorrhoeae* by 4-hydroxyphenylpyruvate provides a basis for selective targeting of a metabolic site. Because Neisseria is unusual in its utilization of 4-hydroxyphenylpyruvate as an inhibitor of prephenate/arogenate dehydrogenase, there is a basis for analog mimics that could not only be very effective but also exceedingly selective against *N. gonorrhoeae*. Thus, analogs of 4-hydroxyphenylpyruvate that inhibit tyrosine biosynthesis can be uniquely effective in *N. gonorrhoeae* and its close relatives.

EXAMPLE 8

N-(phosphonomethyl) glycine, which targets to the sixth pathway enzyme (EPSP synthase) of the aromatic amino acid pathway, produces a severe energy drain because of depletion of PEP and ATP in a variety of bacteria, including *N. gonorrhoeae*. The enzymic target of N-(phosphonomethyl) glycine action is not present in mammalian systems, therefore, N-(phosphonomethyl) glycine is not toxic to the human host. Because N-(phosphonomethyl) glycine acts on an enzyme which is present in pathogenic bacteria but not in the human host, this compound could be used as an effective control agent for bacterial pathogens.

EXAMPLE 9

Even at microgram levels N-(phosphonomethyl) glycine produces a drain upon intracellular supplies of PEP owing to utilization of PEP in massive formation of shikimate-3-phosphate that accumulates behind the blocked enzyme.

Although the initial effect of N-(phosphonomethyl) glycine (inhibition of EPSP synthase) seems to be universal, vulnerability is tied to carbon source (apparently in relationship to PEP levels generated) and to the overall pattern of pathway regulation.

Bacteria are quite diverse in relationship of carbon source to internal PEP levels and to aromatic-pathway patterns of allostery. Thus, knowledge of aromatic-pathway construction and regulation, as well as relationships with carbon-source dissimilation, enhances prospects for designing antimicrobial strategies geared to a particular organism. The existence of novel enzymes or unusual allosteric-control specificities presents opportunities for selective attack of a given organism or group of organisms.

The possibility that N-(phosphonomethyl) glycine sensitivity could be increased by nutritional manipulation could have practical significance. Because N-(phosphonomethyl) glycine causes PEP depletion, other PEP-utilizing pathways become more vulnerable to antimetabolite attack. Thus, synergistic effects can be expected from the use of N-(phosphonomethyl) glycine in combination with other inhibitors. Also, nutritional conditions of carbon sources that decrease PEP levels would enhance sensitivity to N-(phosphonomethyl) glycine.

EXAMPLE 10

L-arogenate is not thus far known to be a regulatory molecule for any microorganism. However, prephenate is a regulatory molecule in many microorganisms—a number of them important pathogens for man. Because L-arogenate is structurally similar to prephenate, a stabilized L-arogenate molecule could disrupt the microorganism's metabolism without affecting human hosts. Therefore, stabilized derivatives L-arogenate could be used as antibiotic agents against organisms such as Staphylococcus.

Prephenate itself can also be modified chemically to generate analog structures. This could be accomplished enzymatically. For example, lactate dehydrogenase converts the pyruvyl sidechain of prephenate to a lactyl sidechain just as it converts phenylpyruvate to phenyllactate. Because man has no pathways for aromatic biosynthesis, antibiotics that target this pathway have ideal selective features for action against the pathogen without affecting the host.

We claim:

1. A method for identifying and producing agents for the selective control of microbial or plant targets, said method comprising:
   i. identifying a difference which exists between an amino acid metabolic pathway of the microbial or plant target and any non-target specie; and
   ii. preparing a control agent which, when applied to said microbial or plant target in the presence of said non-target species, perturbs said amino acid metabolic pathway of said target species but does not significantly perturb the metabolism of said non-target species; wherein said control agent is either a natural compound or an analog of a natural compound.

2. The method, according to claim 1, wherein said amino acid metabolic pathway difference comprises the existence of a metabolic pathway in the target microbe or plant where said metabolic pathway does not exist in the non-target plants or animals.

3. The method, according to claim 2, wherein said metabolic pathway is a pathway which leads to the production of an aromatic amino acid.

4. The method, according to claim 1, wherein said control agent exerts its detrimental effect by blocking a metabolic pathway thus preventing the formation of essential metabolic compounds.

5. The method, according to claim 1, wherein said control agent exerts its detrimental effect by causing the excessive production of pathway intermediates, thus draining energy from the microbial or plant target.

6. The method, according to claim 1, wherein said control agent is an antimetabolite.

7. The method, according to claim 1, wherein said control agent is a mimic of a regulatory molecule.

8. The method, according to claim 1, wherein said control agent is a derivative of either a substrate or a regulatory molecule, said derivative being stable and capable of permeating into the appropriate cells.

9. A method wherein bacterial pathogens on a mammalian host are controlled though the application of N-(phosphonomethyl) glycine, and a second compound causing an energy drain.

10. The method, according to claim 9, where said bacterial pathogen is *N. gonorrhoeae* or *N. meningitidis*.

11. The method, according to claim 9, where N-(phosphonomethyl) glycine and said second compound are applied in conjunction with nutritional manipulation of the pathogen's environment.

* * * * *